United States Patent [19]

Miksza, Jr.

[11] Patent Number: 4,532,927

[45] Date of Patent: Aug. 6, 1985

[54] TWO-PIECE TISSUE FASTENER WITH NON-REENTRY BENT LEG STAPLE AND RETAINING RECEIVER

[75] Inventor: Anthony Miksza, Jr., Jersey City, N.J.

[73] Assignee: Ethicon, Inc., Somerville, N.J.

[21] Appl. No.: 506,087

[22] Filed: Jun. 20, 1983

[51] Int. Cl.³ .............................................. A61B 17/04
[52] U.S. Cl. .......................... 128/334 C; 227/DIG. 1
[58] Field of Search .......... 128/346, 337, 335, 334 R, 128/334 C, 330, 325, 326, 92 B; 3/1; 227/DIG. 1, 15-18, 77; 411/469, 451, 360, 501, 506, 362-364, 455-457; 24/543, 518, 614, 623, 703, 297, 150 FP, 16 PB, 697, 580, 581, 584, 453, 30.5 P, 537, 515, 513, 503, 94-96

[56] References Cited

U.S. PATENT DOCUMENTS

| | | | |
|---|---|---|---|
| Re. 27,391 | 6/1972 | Merser | 24/150 FP X |
| 306,479 | 10/1884 | Goddard | 24/95 |
| 389,660 | 9/1888 | Mandel et al. | 411/457 X |
| 579,831 | 3/1897 | Ketchum | 24/95 |
| 1,988,233 | 1/1935 | Berendt | 24/95 |
| 2,794,981 | 6/1957 | Brayton | 227/15 |
| 2,881,762 | 4/1959 | Lowrie | 128/337 |
| 2,897,561 | 8/1959 | Megibow | 24/95 |
| 2,900,696 | 8/1959 | Bacon | 24/614 X |
| 3,009,852 | 11/1969 | Gruner | 128/330 X |
| 3,166,072 | 1/1965 | Sullivan | 128/346 X |
| 3,210,820 | 10/1965 | Humiston | 24/584 X |
| 3,326,217 | 6/1967 | Kerr | 227/DIG. 1 C X |
| 3,357,296 | 12/1967 | Lefever | 128/334 C X |
| 3,494,006 | 2/1970 | Brumlik | 411/456 X |
| 3,570,497 | 3/1971 | Lemole | 128/335.5 |
| 3,577,601 | 5/1971 | Mariani et al. | 24/16 |
| 3,683,927 | 8/1972 | Noiles | 128/326 X |
| 3,744,495 | 7/1973 | Johnson | 128/330 |
| 3,802,438 | 4/1974 | Wolvek | 128/335 |
| 3,857,396 | 12/1974 | Hardwick | 128/335 |
| 3,875,648 | 4/1975 | Bone | 227/19 X |
| 3,981,051 | 9/1976 | Brumlik | 411/456 X |
| 4,006,747 | 2/1977 | Kronenthal et al. | 128/337 X |
| 4,038,725 | 8/1977 | Keefe | 24/150 FP |
| 4,060,089 | 11/1977 | Noiles | 128/337 X |
| 4,235,238 | 11/1980 | Ogiu et al. | 128/335 X |
| 4,259,959 | 4/1981 | Walker | 128/337 |
| 4,294,255 | 10/1981 | Geroc | 128/334 C |
| 4,326,531 | 4/1982 | Shimonaka | 128/326 |
| 4,400,833 | 8/1983 | Kurland | 3/1 |
| 4,402,445 | 9/1983 | Green | 128/334 R X |
| 4,454,875 | 6/1984 | Pratt et al. | 128/92 B |

FOREIGN PATENT DOCUMENTS

| | | | |
|---|---|---|---|
| 1097171 | 3/1981 | Canada | 128/330 |
| 1385691 | 12/1964 | France | 40/300 |
| WO83/01190 | 4/1983 | PCT Int'l Appl. | 227/DIG. 1 |
| 82738 | 10/1919 | Switzerland | 128/330 |
| 972731 | 10/1964 | United Kingdom | 128/346 |

*Primary Examiner*—Michael H. Thaler
*Attorney, Agent, or Firm*—Robert L. Minier

[57] ABSTRACT

A fastener is provided to hold together separated portions of mammalian tissue and includes an open loop fastening member and a receiver adapted to receive the legs of the fastening member. Each fastening member leg extends through the receiver and the distal end of the leg is bent back into a base structure of the receiver to effect engagement of the fastening member and receiver. In the fully engaged configuration, the distal end of each bent leg does not project from the receiver and does not penetrate the tissue portions.

7 Claims, 3 Drawing Figures

TWO-PIECE TISSUE FASTENER WITH NON-REENTRY BENT LEG STAPLE AND RETAINING RECEIVER

CROSS-REFERENCE TO RELATED PATENT APPLICATION

The disclosures of this patent application are related to the disclosures in the concurrently filed patent application of James Bedi entitled "Two-Piece Tissue Fastener With Bent Leg Staple And Retaining Receiver," Ser. No. 506,083.

TECHNICAL FIELD

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International patent application No. PCT/SU79/00049 discloses a variety of fastening devices and instruments for performing circular anastomoses on the large intestine. The aforementioned disclosures serve as examples of a wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The fastener strip prongs each include a plurality of spaced-apart engaging members for engaging the retainer strip at a desired position relative to the prongs. This provides for the capability of adjusting the distance between the fastener strip and the retainer strip. Such a fastening device may be fabricated from a biodegradable or absorbable material.

Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

Further, it would be beneficial if such an improved fastener had a configuration that would enable the fastener to be fabricated with (1) as small a size as possible to minimize dosage and (2) with a minimum of sharp edges or protrusions. Also, another desirable feature of such an improved fastener would be a fastener configuration that would pass easily through tissue and that would not form, or contribute to the formation of, pockets of infection in the tissue.

Further, such an improved fastener would desirably provide the surgeon with tactile feedback and compensating control during the application of the fastener.

Finally, such an improved fastener should have the capability for maintaining the tissue portions in approximation and compression for a minimum of 21 days in vivo.

It would also be advantageous to provide such a fastener with a design that would facilitate its application to the tissue portions with a simple yet effective method. It would also be desirable if the improved fastener could readily accommodate application by means of an appropriately designed instrument.

An improved fastener known to the inventor, comprising a generally U-shaped staple-like fastening member and multi-passage receiver, is disclosed in the concurrently filed patent application of James Bedi entitled "Two-Piece Tissue Fastener With Bent Leg Staple And Retaining Receiver," Ser. No. 506,083. The legs of the fastening member are passed from one side of the tissue portions through the tissue portions and bent into engagement with the receiver on the other side of the tissue portions. In a specific form of the fastener claimed in that application, the end of each fastening member leg is passed through one primary passage extending between first and second sides of the receiver and is bent back into a secondary passage that also extends between the first and second sides of the receiver. With this type of structure the distal ends of the fastening member legs can project back out of the receiver and into the tissue to provide increased tissue holding action. In some situations, however, this may be undesirable (e.g., where it is deisred to minimize tissue penetration damage). With respect to such a potentially undesirably feature, the novel fastener of the present invention which is described hereinafter can be regarded as an improvement over the above-discussed fastener embodiment of the above-referenced concurrently filed patent application of James Bedi.

SUMMARY OF THE INVENTION

An improved fastener is provided to hold together portions of mammalian tissue, such as are defined by a wound or incision, to facilitate healing of the wound or incision. The fastener comprises an open loop fastening member which has a pair of legs adapted to penetrate two overlapped tissue portions and which has a link connecting the legs. The link is adapted to lie substantially against one of the tissue portions.

A receiver is provided for being disposed against the other of the tissue portions opposite the fastening member and has means for receiving the fastening member legs in a bent configuration after the legs have been inserted through the tissue portions. A leg guide means or member is provided for at least temporarily guiding the fastening member legs into the bent configuration.

To join the tissue portions with the fastener, the two tissue portions are first approximated in a generally face-to-face relationship. Next, the fastening member is positioned on one side of the tissue portions with the legs oriented at an appropriate angle to penetrate the tissue portions. The receiver is positioned on the other side of the tissue portions opposite the fastening member and generally in alignment with the fastening member legs. The guide member is disposed against the side of the receiver facing away from the tissue portions.

Next, relative movement is effected between the fastening member on the one hand and the tissue portions, receiver, and guide member on the other hand to cause penetration of the tissue portions by the fastening member legs and to cause a portion of each of the fastening member legs to pass through the receiver and to be redirected back into the receiver. The relative movement is effected until the link is disposed against the surface of one of the tissue portions and until the receiver is disposed against the other of the tissue portions with the fastening member legs each bent in the receiver. This prevents separation of the fastening member and receiver. In the fully engaged configuration, the distal end of each bent leg does not project from the receiver and does not penetrate the tissue portions.

Numerous other features of a novel tissue fastener will be apparent from the following detailed description and accompanying drawings.

BRIEF DESCRIPTION OF THE DRAWINGS

In the accompanying drawings forming part of the specification, and in which like numerals are employed to desginate like parts throughout the same.

DESCRIPTION OF THE PREFERRED EMBODIMENT

This invention may be used in many different forms. The specification and accompanying drawings disclose only one specific form as an example of the use of the invention. The precise shapes and sizes of the components herein described are not essential to the invention unless otherwise indicated. The invention is not intended to be limited to the embodiment illustrated, and the scope of the invention will be pointed out in the appended claims.

Figure 1:
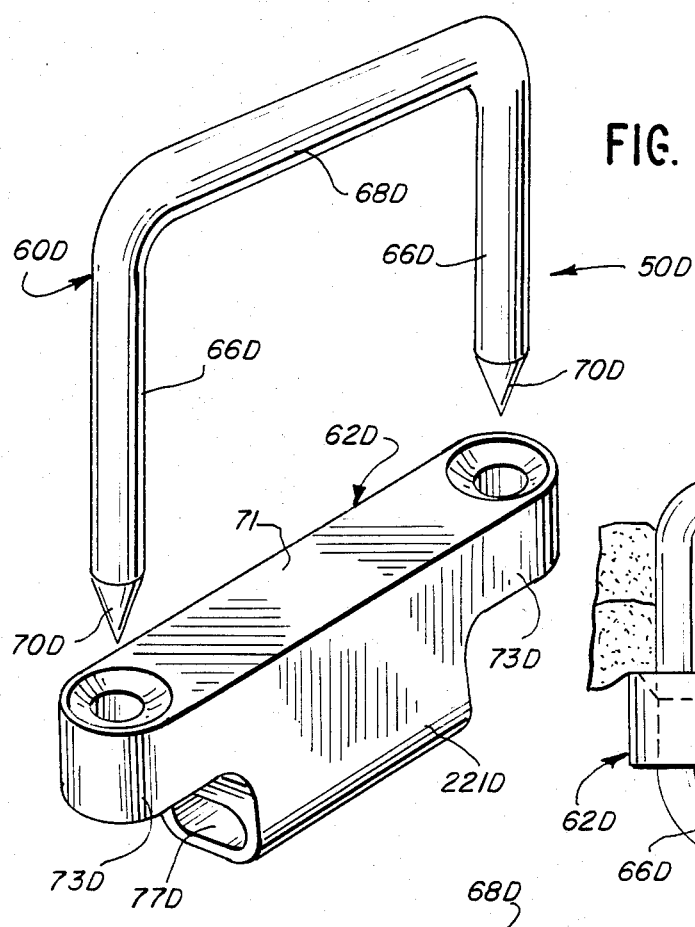
FIG. 1 is a perspective view of the fastener of the present invention which includes a fastening member and receiver.
Figure 3:
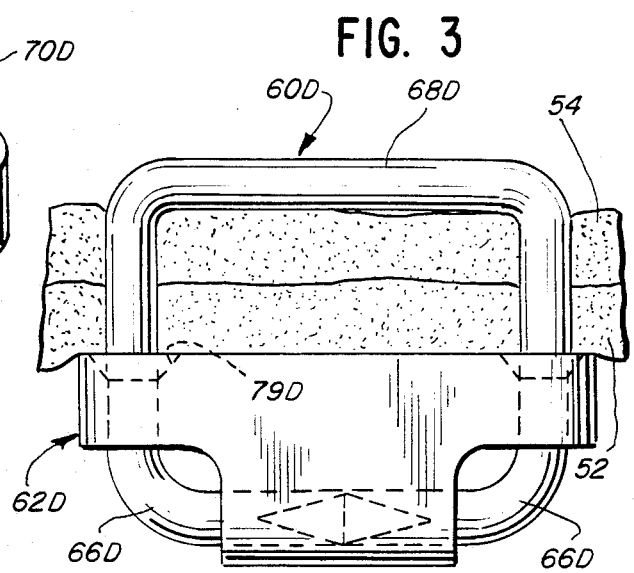
FIG. 3 is a view similar to FIG. 2 but showing the fastening member and receiver fully engaged after the leg guide member has been removed from the site.
Figure 2:
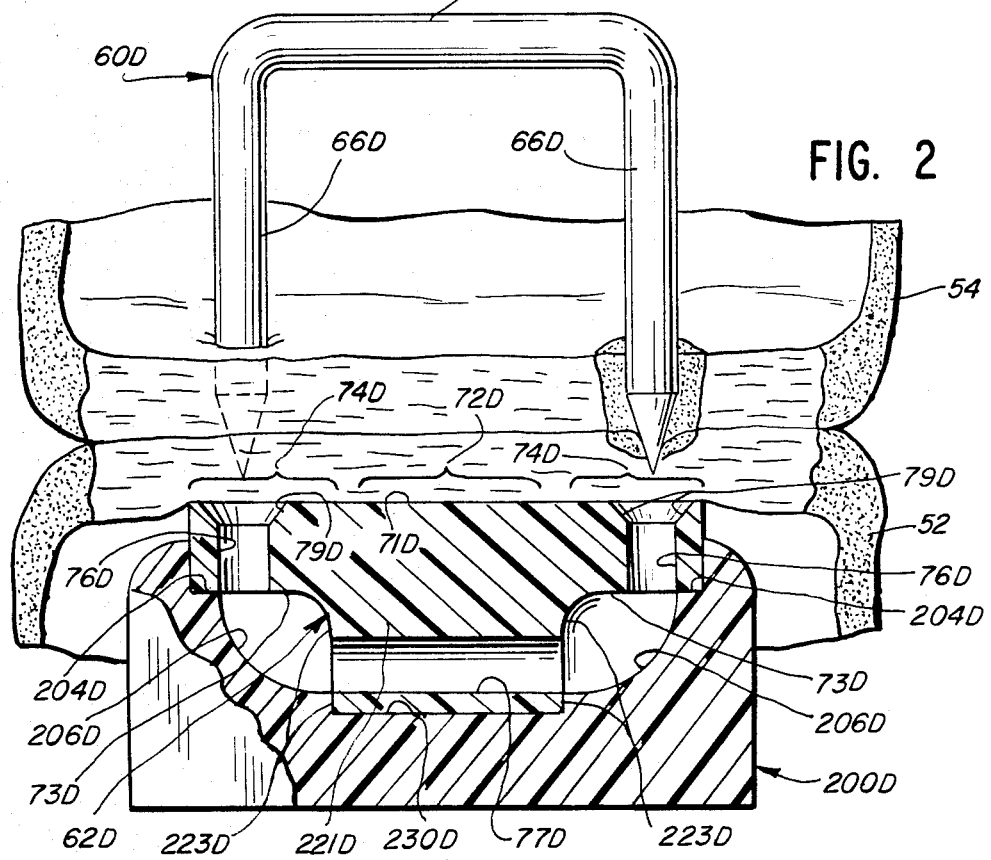
FIG. 2 is a fragmentary, partial cross-sectional view of two portions of mammalian tissue defined by an incision or wound with some of the tissue cut away to better show interior detail and illustrating (1) the fastening member of FIG. 1 being inserted into the two portions of the tissue, and (2) the receiver of FIG. 1 being held against the tissue portions by a leg guide member.

The fastener is illustrated in FIGS. 1-3 and is designated generally therein by reference numeral 50D. The individual parts of the fastener 50D are shown separately in FIG. 1. The fastener 50D is illustrated in FIG. 3 in the fully assembled, "set" configuration wherein it is shown holding together two portions 52 and 54 of mammalian tissue, such as are defined by a wound or incision, to facilitate healing of the wound or incision. Typically, a plurality of such fasteners 50D would be used to close a wound or incision. However, with just a small wound or incision, one fastener 50D may be sufficient.

The fastener 50D includes at least two components, a generally U-shaped or open loop fastening member 60D and a receiver 62D. The two components are initially separated as illustrated in FIG. 1 and are adapted to cooperate to compress or hold between them the tissue portions 52 and 54 as illustrated in FIG. 3.

As is best illustrated in FIG. 1, the fastening member 60D includes (1) a pair of legs 66D adapted to penetrate the tissue portions and (2) a link 68D which is connected to the legs 66D and which is adapted to lie substantially against one of the tissue portions (e.g., tissue portion 54 in FIG. (3). The link 68D may be cylindrical or may have any other suitable shape (such as that of a regular parallepiped, for example). The legs 66D of the fastening member 60D are generally parallel to each other and are generally perpendicular to the link 68D. Preferably, each leg 66D has a solid, generally cylindrical configuration with a conical end 70D to facilitate or aid in the penetration of the tissue portions.

The legs 66D need not be necessarily be cylindrical as illustrated but may have a non-circular cross-section. Preferably, however, the legs 66D are capable of being bent along a relatively small curvature for purposes that will become apparent hereinafter. To this end, it has been proposed that each leg 66D may be fabricated from a suitable material, such an extruded 0.025 inch diameter rod of thermoplastic polymer material. One such suitable material is a copolymer of lactide and glycolide. It has been demonstrated that an extruded rod of this material having a diameter of 0.025 inch is capable of being bent along an arc of a 0.030 inch diameter circle without failure.

The receiver 62D has a major first side 71D which is adapted to be placed against one of the tissue portions and has an oppositely facing major second side 73D. The receiver 62D can also be regarded as having a pair of leg receiving members 74D (designated in FIG. 2 only). The receiving members 74D can be regarded as being joined by a central portion 72D (designated in FIG. 2 only). Each leg receiving member 74D has a first side that is part of the receiver's major first side 71D and has a second side that is part of the receiver's major second side 73D.

Each leg receiving member 74D defines a first passage 76D extending between the receiver's major first side 71D and the receiver's major second side 73D. Each first passage 76D is adapted to receive a portion of one of the fastening member legs 66D. Preferably, as best illustrated in FIG. 2, the receiver 62D defines an enlarged, frustoconical surface 79D on the receiver's major first side 71D at each primary passage 76D to facilitate entry of the fastening member legs 66D.

The receiver 62D defines at least one additional or secondary passage or cavity 77D for receiving another portion of each of the fastening member legs 66D. Specifically, the receiver 62D includes an outwardly extending base 221D on the receiver second side 73D between the two primary passages 76D. The base 221D can also be regarded as lying between, and projecting outwardly from, the second sides of the leg receiving members 74D.

The base 221D has oppositely facing end walls 223D (designated in FIG. 2 only). The additional or secondary passage or cavity 77D is defined in base 221D and extends between the base end walls 223D. Preferably, the first passages 76D of the leg receiving members 74D have generally parallel longitudinal axes, and the additional or secondary passage 77D has a longitudinal axis oriented generally normal to the longitudinal axes of the receiver first passages 76D. As best illustrated in FIGS. 1 and 3, the secondary passage 77D has a size and shape to accommodate the distal ends of both the fastening member legs 66D in side-by-side relationship.

The receiver 62D may be formed from the same material or materials as the fastening member 60D. For example, the receiver may be molded from an absorbable polymer such as a copolymer of lactide and glycolide.

The fastener 50D may also be regarded, in one sense, as further including a leg guide member 200D (illustrated in FIG. 2 only) for temporarily cooperating with the fastening member 60D and with the receiver 62D at the wound or incision when the fastening member and receiver are applied to the tissue portions in a manner described in detail hereinafter. After application of the fastening member 60D and the receiver 62D to the tissue portions, the leg guide member 200D is removed from the site and no longer forms a part of the structure of the assembled fastener 50D (FIG. 3).

The guide member 200D may also be integrally formed within the jaw of a suitable instrument (not illustrated) for applying the fastening member 60D and the receiver 62D. In such a case, the leg guide member 200D could be properly characterized as being separate from, and not part of, the fastener 50D per se.

In any event, the guide member 200D has a bearing side 204D for bearing against the major second side 73D of the receiver 62D. The leg guide member 200D is adapted to be disposed adjacent the major second side 73D of the receiver 60D and is adapted to direct the distal end of each leg 66D of the fastening member 60D at the receiver major second side 73D from the primary or first passage 76D and into the additional or secondary passage 77D. The guide member 200D also functions to guide intermediate portions of the legs extending between the receiver first or primary passages 76D and the additional or secondary passages 77D as relative movement is being effected between the fastening member 60D and the receiver 62D.

The guide member 200D preferably includes a recessed portion or cavity 230D for receiving the bottom of the receiver base 221D. In addition, the guide member 200D includes a guiding means for directing each leg 66D in the proper path. The guiding means is defined in the guide member 200D as a channel 206D opening to the engaging side 204D of the guide member 200D. There are two such channels 206D spaced apart in the guide member 200D. The bottom of each channel 206D is defined in the guide member 200D by a generally quarter-cylindrical surface that is designed to effect a 90° change of direction and bend in the fastening member leg 66D.

Preferably, the bottom of each channel 206D is elevated above the bottom of the cavity 230D by an amount that brings the receiver second passage 77D into alignment with the channel 206D when the receiver 62D is properly received in the guide member 200D.

During application of the fastener 50D to join the tissue portions, the receiver 62D is mounted in the guide member 200D (which in turn may be mounted in the jaw of a suitable instrument (not illustrated) or which may be an integral part of the jaw of such an instrument). Such an instrument may have a second jaw for holding the fastenening member 60D initially spaced from the receiver 62D. The instrument could also include a suitable drive mechanism for effecting relative movement between the fastening member 60D on the one hand and the receiver 62D and guide member 200D on the other hand, so as to bring the fastening member legs 66D into the receiver 62D.

When joining the tissue portions 52 and 54 with the fastener 50D, the tissue portions are first approximated in surface-to-surface relationship as illustrated in FIG. 2. Next, the fastening member is positioned on one side of the tissue portions with the legs 66D oriented at an appropriate angle to penetrate the tissue portions. This may be effected with a suitable instrument for holding the fastening member 60D as discussed above. At the same time, the receiver 62D is held in the guide member 200D on the other side of the tissue portions opposite the fastening member 60D with the first passages 76D generally in alignment with the fastening member legs 66D.

As illustrated in FIG. 2, the receiver 62D is initially held directly against one of the tissue portions by the leg guide member 200D. Then relative movement is effected between the fastening member 60D on the one hand and the receiver 62D and guide member 200D on the other hand, so as to cause the fastening member legs 66D to penetrate the tissue portions and to become properly engaged with the receiver 62D.

Once the fastening member legs 66D have been driven through the tissue portions and properly engaged with the receiver 62D, the guide member 200D may be removed from the site of the wound or incision to leave the remaining fastener elements in the engaged orientation illustrated in FIG. 3 wherein the tissue portions 52 and 54 are joined together.

As best illustrated in FIG. 3, the distal ends of the fastening member legs 66D are partially overlapped and aligned in side-by-side relationship. However, it is not necessary that the legs be arranged in such an overlapping configuration. If desired, the secondary passage 77D may be of a size and shape to accommodate each leg 66D in sliding engagement and in end-to-end relationship. Owing to the approximately 90° bend in each of the fastening member legs 66D, the fastening member 60D cannot be pulled out of the receiver 62D.

Although the legs 66D of the fastener 50D are illustrated as being retained in the receiver 62D with a substantially 90° bend, it is to be realized that the legs may be bent more or less than this amount and retained within one or more suitable secondary passages in the receiver 62D. The secondary passage 77D of the receiver 66D is illustrated as extending completely through the receiver base 221D between the base end walls 223D. This secondary passage 77D may also be characterized as comprising two cavities or passages that extend from either end wall 223D and that join or meet within the base 221D. As an alternative, two unconnected, separate passages or cavities, each extending only part way into the receiver base 221D from each endwall 223D, may be provided instead. Each such passage or cavity would receive the distal end of one of the fastening member legs 66D.

Such separate passages or cavities may be aligned in generally end-to-end relationship. However, such separate passages or cavities may instead be angled toward the same point or may be angled along different axes in the receiver base 221D. In any case, the term "passage" as used in this specification and in the claims is intended to include a suitable fastening member leg receiving hole or cavity, regardless of whether or not such a cavity extends completely through the receiver base from one end wall of the receiver base to the other end wall of the receiver base.

It is also to be noted from FIG. 3 that the distal ends 70D of the fastening member legs 66D are directed back into the receiver base 221D and not back into the tissue portions. Thus, there is less of a chance that the tissue portions will be subjected to further damage or trauma.

Further, only gently curving portions of the legs protrude from the receiver 62D. Thus, there are no sharp leg ends projecting outwardly of the tissue portions where surrounding tissue or organs may be damaged. Consequently, there is no portion of each leg of the fastening member 60D that must be severed to insure that an adjacent tissue or organ is not injured.

It is seen that the fastener 50D can accommodate various thicknesses of tissue. The fastening member 60D may be inserted into the receiver 62D and relative movement may be effected between the two components until the desired tissue compression is achieved. The components are prevented from pulling apart as soon as the fastener legs have been bent and guided at least partly into the additional (secondary) passage or passages 77A. Thus, a wide range of adjustability is conveniently provided.

ALTERNATIVE DESIGN FEATURES

In the figures, the two legs of the fastening member are connected by a portion of the fastening member (e.g., the link or clamping member) which is illustrated as being generally straight and extending perpendicular to the two legs. The structure need not be limited to such a shape however. Instead, all or a portion of the length of the fastening member between the two legs may be arched or arcuate or may include an arcuate portion (e.g., an inverted U-shaped configuration). This would function to initially provide a free space between the upper tissue portion and the top of the fastening member to allow for some expansion of the tissue.

However, in those situations where increased initial tissue compression is desired, a modified receiver structure may be provided to cooperate with the above-described arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

From the foregoing, it will be observed that numerous variations and modifications may be effected without departing from the true spirit and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A fastener adapted to hold together two portions of mammalian tissue, such as are defined by a wound or incision, to facilitate healing of the wound or incision, said fastener comprising:

an open loop fastening member, said fastening member comprising a pair of first and second legs with distal ends adapted to penetrate said tissue portions and a link connecting said legs that is adapted to lie substantially against one of said tissue portions; and a receiver adapted to be disposed against the other of said tissue portions opposite said fastening member; said receiver having a leg receiving member for receiving one of said fastening member legs after said legs have been inserted through said tissue portions and having another leg receiving member for receiving the other of said fastening member legs after said legs have been inserted through said tissue portions; each of said leg receiving members having a first side adapted to be placed against one of said tissue portions and having a generally oppositely facing second side; each of said leg receiving members defining a first passage extending between said first and second sides of said leg receiving member for receiving a portion of one of said fastening member legs; said receiver having a base between, and projecting outwardly from, said second sides of said leg receiving members; said base defining end walls projecting outwardly from said second sides of said leg receiving members; said base further having an additional passage or cavity extending completely through said base from one of said end walls to the other of said end walls for receiving another portion of each of said legs whereby a means for guiding said legs may be at least temporarily disposed adjacent said receiver for (1) directing the distal end of each of said legs at said leg receiving members second side from one of said first passage into said additional passage or cavity and (2) guiding said legs between said first passages and said additional passage or cavity as relative movement is effected between said fastening member and said receiver.

2. The fastener in accordance with claim 1 in which said fastener further specifically includes a leg guide member functioning as said leg guiding means for temporarily being used with said fastening member and said receiver during application of the fastening member and receiver to the tissue portions;

in which said leg guide member has a bearing side for bearing against at least a portion of said second side of each said receiving member;

in which said leg guide member defines at least one channel opening to said bearing side; and in which said leg guide member has a generally quarter-cylindrical concave surface defining the bottom of said channel.

3. The fastener in accordance with claim 1 in which said additional passage or cavity has a size and shape to accommodate distal end portions of said fastening member legs in side-by-side relationship.

4. The fastener in accordance with claim 3 in which said first passages are generally parallel and in which said additional passage or cavity is generally normal to said first passages.

5. A fastener adapted to hold together two portions of mammalian tissue, such as are defined by a wound or incision, to facilitate healing of the wound or incision, said fastener comprising:

an open loop fastening member, said fastening member comprising a pair of first and second legs with distal ends adapted to penetrate said tissue portions and a link connecting said legs that is adapted to lie substantially against one of said tissue portions; and a receiver for receiving said fastening member legs after said legs have been inserted through said tissue portions; said receiver having a first side adapted to be placed against one of said tissue portions and having a generally oppositely facing second side; said receiver having a primary passage extending between said first and second sides of said receiver for receiving a portion of said first leg, said receiver having another primary passage extending between said first and second sides of said receiver for receiving a portion of said second leg; said receiver having an outwardly extending base on said second side between said two primary passages; said base having two end walls; said receiver defining a secondary passage or cavity extending between said base end walls for receiving other portions of both of said first and second legs whereby a means for guiding each said fastening member leg may be at least temporarily disposed adjacent said receiver second side for directing the distal end of each said legs at said receiver second side from one of said primary passages into said secondary passage or cavity and for guiding each said leg between one of said primary passages and said second passage or cavity as relative movement is effected between said fastening member and said receiver.

6. The fastener in accordance with claim 5 in which said receiver base defines a secondary passage or cavity extending between said base end walls for receiving in side-by-side relationship said other portions of each of said first and second legs.

7. The fastener in accordance with claim 6 in which said receiver base end walls are generally oppositely facing.

* * * * *